United States Patent
Dadlani Mahtani et al.

(10) Patent No.: US 10,039,957 B2
(45) Date of Patent: Aug. 7, 2018

(54) GOGGLES, SYSTEM AND METHOD FOR PROVIDING FEEDBACK

(75) Inventors: Pavankumar Murli Dadlani Mahtani, Eindhoven (NL); Warner Rudolph Theophile Ten Kate, Eindhoven (NL); Jochen Renaat Van Gheluwe, Eindhoven (NL); Kars-Michiel Lenssen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 126 days.

(21) Appl. No.: 13/878,271

(22) PCT Filed: Sep. 20, 2011

(86) PCT No.: PCT/IB2011/054115
§ 371 (c)(1),
(2), (4) Date: Apr. 8, 2013

(87) PCT Pub. No.: WO2012/046156
PCT Pub. Date: Apr. 12, 2012

(65) Prior Publication Data
US 2013/0187786 A1    Jul. 25, 2013

(30) Foreign Application Priority Data

Oct. 8, 2010 (EP) .................................. 10186934

(51) Int. Cl.
*A63B 33/00* (2006.01)
*A61F 9/02* (2006.01)
*A63B 71/06* (2006.01)

(52) U.S. Cl.
CPC ............ *A63B 33/002* (2013.01); *A61F 9/029* (2013.01); *A63B 71/0622* (2013.01); *A63B 2071/0666* (2013.01); *A63B 2225/50* (2013.01)

(58) Field of Classification Search
CPC ............. A61F 9/029; A63B 2071/0666; A63B 2225/50; A63B 33/002; A63B 71/0622
See application file for complete search history.

(56) References Cited

U.S. PATENT DOCUMENTS 2,928,097 A    3/1960  Neufeld
3,944,345 A    3/1976  Decorato
(Continued)

FOREIGN PATENT DOCUMENTS

DE    202005010966 U1    10/2006
DE    102009060638 A1    1/2011
(Continued)

OTHER PUBLICATIONS

Trevor Jones, "STING RAE: Swimming Training Interactive Goggles for Real-time Aquatic", Computing Department, Lancaster University, Bailrigg, Lancaster, England. LA1 4YR, 2000.
(Continued)

*Primary Examiner* — Quan-Zhen Wang
*Assistant Examiner* — Rajsheed Black-Childress
(74) *Attorney, Agent, or Firm* — Larry Liberchuk

(57) ABSTRACT

The present invention relates to goggles (10) for providing feedback, in particular to a user, comprising at least one transparent portion (14) forming at least a portion of at least one glass (14) of the goggles (10), display means (18) for displaying light signals, wherein the display means (18) are integrated in the transparent portion (14), cover a surface of the transparent portion (14) at least partially and/or cover a surface of a frame (12) of the goggles (10) around the glass (14) at least partially, drive means (20) coupled to the display means (18) for providing signals to the display means (18) corresponding to the light signals to be displayed.

14 Claims, 9 Drawing Sheets

(56) References Cited

U.S. PATENT DOCUMENTS

| | | | |
|---|---|---|---|
| 5,224,772 A | | 7/1993 | Fustos |
| 5,446,506 A | | 8/1995 | Dawklins |
| 5,585,871 A | * | 12/1996 | Linden ............... A63B 71/0686 351/158 |
| 5,805,267 A | * | 9/1998 | Goldman ............ A61N 5/0618 351/200 |
| 6,006,367 A | | 12/1999 | Webster |
| 6,009,564 A | | 1/2000 | Tackles |
| 6,204,974 B1 | * | 3/2001 | Spitzer ................ G02B 27/017 359/630 |
| 6,356,392 B1 | * | 3/2002 | Spitzer ................ G02B 27/017 345/8 |
| 6,431,705 B1 | * | 8/2002 | Linden .................. G02C 11/00 351/158 |
| 6,447,115 B1 | | 9/2002 | Gallagher |
| 6,704,935 B1 | * | 3/2004 | MacDonald ...................... 2/15 |
| 6,824,265 B1 | | 11/2004 | Harper |
| 7,081,809 B1 | | 7/2006 | Mix |
| 8,272,758 B2 | * | 9/2012 | Meir et al. .................... 362/231 |
| 8,388,127 B2 | | 3/2013 | Han |
| 8,588,053 B2 | | 11/2013 | Watanabe |
| 8,702,430 B2 | | 4/2014 | Dibenedetto |
| 8,717,254 B1 | * | 5/2014 | Nave et al. ...................... 345/8 |
| 9,242,142 B2 | | 1/2016 | Vincent |
| 2001/0021108 A1 | | 9/2001 | Shimada |
| 2003/0189484 A1 | | 10/2003 | Rust |
| 2005/0036100 A1 | * | 2/2005 | Rice et al. ...................... 351/62 |
| 2005/0099798 A1 | | 5/2005 | Cugini |
| 2005/0225867 A1 | | 10/2005 | Ishibashi |
| 2005/0225868 A1 | | 10/2005 | Nelson |
| 2006/0012975 A1 | | 1/2006 | Huttner |
| 2008/0018532 A1 | | 1/2008 | MacKintosh |
| 2008/0055541 A1 | * | 3/2008 | Coulter et al. ................ 351/169 |
| 2008/0151179 A1 | | 6/2008 | Howell |
| 2008/0316605 A1 | * | 12/2008 | Hazell et al. ................. 359/630 |
| 2010/0013818 A1 | * | 1/2010 | Akai et al. ..................... 345/212 |
| 2010/0030482 A1 | * | 2/2010 | Li .................... 702/19 |
| 2010/0134297 A1 | | 6/2010 | Baldwin |

FOREIGN PATENT DOCUMENTS

| | | |
|---|---|---|
| FR | 2806312 A1 | 9/2001 |
| GB | 2438223 A | 11/2007 |
| JP | H049166 A | 1/1992 |
| JP | H06230322 A | 8/1994 |
| JP | H08122063 H | 5/1996 |
| JP | 2007503008 A | 2/2007 |
| JP | 4009166 B2 | 11/2007 |
| WO | WO2008033689 A2 | 3/2008 |
| WO | WO2008065614 A1 | 6/2009 |
| WO | WO2011067719 A1 | 6/2011 |

OTHER PUBLICATIONS

K.-M.H. Lenssen et al., "Bright Color Electronic Paper Technology and its Applications", Proceedings IDW'09, pp. 529-532 (2009).

Forster et al., "Non-Interrupting User Interfaces for Electronic Body-Worn Swim Devices", Proceedings of Ubicomp 2009.

"Password", Issue 36, Nov. 2009, pp. 23-25, http://www.research.philips.com/password/download/password_36.pdf.

K.-M.H. Lenssen, "Novel Concept for Full-Color Electronic Paper", J. of the SID 17/4, Journal of the Society for Information Display, 2009, pp. 383-388.

Bachlin, M. et al., "SwimMaster: A Wearable Assistant for Swimmer". In Proceedings of UbiComp 2009, Sep. 30-Oct. 3, 2009, Orlando, Florida, USA.

\* cited by examiner

GOGGLES, SYSTEM AND METHOD FOR PROVIDING FEEDBACK

FIELD OF THE INVENTION

The present invention relates to goggles, a system and a method for providing feedback.

BACKGROUND OF THE INVENTION

Goggles or glasses of this kind are known from German application DE 20 2005 010 966 U1. The goggles described in that publication provide light signals to a user, wherein light sources are located in the frame of the goggles. The light sources provide light spots directed to the eyes of the user to provide signals or feedback to the user.

A similar arrangement is known from Förster et al., "Non-interrupting user interfaces for electronic body-worn swim devices", proceedings of Ubicomp 2009. These goggles or glasses comprise bi-color LEDs at the frame and a receiving unit for remotely receiving signals to be provided as light signals to the eyes of the user. Thus, a second person e.g. a coach can provide instructions or feedback to a swimming person to improve the coaching.

The disadvantage of the goggles or glasses known from the prior art is that the light sources do not provide a uniform distribution of light and the user may miss the signals or may get confused looking into the LEDs light spot. The LEDs may also cause glare for the users since the LEDs shining on them. Further, the LEDs mounted on the outside of the frame of the goggles may cause a higher drag and may be uncomfortable for the swimmer. Finally, the known solutions are not aesthetic in the sense that such aesthetic solution cannot be provided because of the LED mounting in the line of sight of the user's eyes.

SUMMARY OF THE INVENTION

It is an object of the present invention to provide goggles, a system and a method for providing feedback, in particular to a user that is more comfortable. Further, a solution that consumes less power is preferably desired.

In a first aspect of the present invention goggles for providing feedback, in particular to a user are presented, comprising:
 at least one transparent portion forming at least a portion of at least one glass or lens of the goggles,
 display means for displaying light signals,
 wherein the display means are integrated in the transparent portion or in a frame of the goggles, cover the surface of the transparent portion at least partially, and/or cover a surface of the frame of the goggles around the glass at least partially and
  drive means coupled to the display means or the transparent portion for providing signals to the display means corresponding to the light signals to be displayed.

In a further aspect of the present invention a system is presented for providing feedback, in particular to a user, comprising:
 feedback means for providing a feedback signal,
 transmission means coupled to the feedback means for transmitting the feedback signal to receiving means coupled to the goggles mentioned above.

In a further aspect of the present invention a method is presented for providing feedback, in particular to a user, comprising the steps of:

determining at least one physical or physiological parameter of the user,
 processing the determining parameter using background data,
 generating a feedback signal on the basis of the processed data, and
 providing the feedback signal, in particular to a user by means of the goggles mentioned above.

Preferred embodiments of the invention are defined in the dependent claims. It shall be understood that the claim methods have similar and/or identical preferred embodiments as the claimed arrangement and as defined in the dependent claims.

The present invention is based upon the idea to present light signals via display means integrated in the glasses or lenses, covering the glasses or lenses of the goggles as a layer or foil and/or covering a surface of a frame of the goggles around the glasses or lenses on the inside or outside at least partially, e.g. as light guiding means. The advantage of this aspect is that a uniform light distribution is provided and, in particular, that the light signals reach the user independent of the viewing direction.

Further, the second aspect of the present invention is based upon the idea to provide either measurement data like stroke frequency or heartbeat to the user or to provide messages from a second person like a coach to the user by transmitting a signal to receiving means coupled to the goggles. The advantage of this aspect is that the user or the coach can receive different information as feedback to improve the coaching.

The third aspect of the present invention is based upon the idea to process the determined parameters and to provide the processed data to the user or the coach by means of the goggles. The advantage of this aspect is that the user receives continuously feedback from the determining means and/or from the coach or the coach from the determining means.

The light signals are preferably binary light signals of one color or of different colors.

According to a first embodiment of the present invention, goggles for providing feedback, in particular to a user, are provided, comprising
 at least one transparent portion forming at least a portion of at least one glass of the goggles,
 display means for displaying light signals to the user,
 drive means coupled to the display means for providing signals to the display means corresponding to the light signals to be displayed,
 wherein the display means are formed of a continuously at least partially transparent layer, which is integrated in the transparent portion, or which covers the surface of the transparent portion at least partially.

This embodiment is based upon the idea to present light signals via a continuously transparent portion integrated in the glasses or lenses of the goggles or a continuously transparent layer or foil covering the surface of glasses or lenses of goggles. The advantage of this aspect is that a uniform light distribution is provided and that the light signals reach the user independent of the viewing direction.

According to a further embodiment, the display means are formed of an at least partially transparent layer, which is integrated in the transparent portion, or which covers the surface of the transparent portion at least partially.

According to a preferred embodiment receiving means are provided including at least one receiving unit for acquiring signals to be displayed by the display means. The receiving means serve as an interface to other devices in particular to determining means or input means to determine physical and/or physiological parameters of the user or to receive messages from a second person, e.g. a coach to provide certain feedback information to the user. These receiving means provide a comfortable use of the goggles without any connection cable.

According to a further preferred embodiment the drive means comprise a light source for providing the light signals to be displayed and wherein the display means comprise light guiding means for guiding the light signals of the light sources. The light source provides a simple and cheap possibility to provide the light signals and the guiding means provide a simple solution to realize a uniform distribution of the light signals.

According to an alternative embodiment, the transparency and/or the color of the display means is adaptable electrically by means of the signals provided by the drive means. This embodiment provides a more natural appearance of the light signal and has a significantly lower power consumption, since this embodiment uses and modifies the ambient light. The signal provided by the drive means is an electrical signal to adapt the transparency and the color of the display means.

According to an alternative embodiment of the present invention, the display means comprise an organic light emission diode film (OLED). This provides a cheap and comfortable solution, since the OLED provides a uniform light distribution and can be driven by simple drive means.

According to a further embodiment the light guiding means comprise outcoupling structures at the surface and/or in the bulk for scattering the light of the light sources. This provides a cheap and effective mechanism to scatter the light in the light guiding means to provide a uniform light distribution. The outcoupling structures preferably cover less than 10 to 15% of the light guiding means. This provides a high transparency of the light guide.

According to a further embodiment, the light guiding means comprise an at least partially reflective portion or an at least partially diffusely reflective portion for reflecting and/or scattering the light of the light source. This provides an effective mechanism to reflect and/or scatter the light of the light source to the eye of the user.

According to a further embodiment, the drive means comprise a light source coupled to the transparent portion for providing the light signals to be displayed to the display means, and wherein the display means are formed of an at least partially reflective portion or an at least partially diffusely reflective portion. This embodiment is based upon the idea that the transparent portion, e.g. the glass of the goggles, serves as light guiding means and the transparent portion is covered at least partially by a reflective or a diffusely reflective portion, e.g. a diffusely reflective layer, to reflect the light of the light source diffusely to the eye of the user. This embodiment provides a cheap solution to provide feedback to the eye of the user, since a separate light guide is not necessary.

It is preferred to form the reflective portion of a continuous layer, foil or paint. This is a cheap solution to provide a reflective or diffusely reflective portion.

According to a further embodiment, it is preferred to cover the display means by a protective layer or coating. This provides an effective and cheap solution to protect the display means against environmental influences. This increases the durability of the display means.

According to a further embodiment, the drive means comprise a light source coupled to the transparent portion for providing the light signals to be displayed, and wherein the display means comprise outcoupling structures at the surface and/or in the bulk of the transparent portion for scattering the light of the light source. This is a cheap solution to provide the display means, since no separate light guiding means are necessary.

According to a further preferred embodiment, the drive means comprise a light source and the display means are at least partially formed of a frame or frame connecting means connected to the at least one glass or lens of the goggles, wherein the frame and the frame connecting means are formed at least partially of a transparent material. This provides display means which can be assembled with low technical effort and, further, the light signals are also visible from the outside of the goggles so that a feedback can be provided to other people, e.g. a coach.

According to a further embodiment energy supply means for providing electrical power, in particular a solar cell, receiving means for receiving electrical power via contactless energy transfer and/or kinetic energy conversion means for converting movements of the goggles into electrical power. A solar cell, which may be connected to the frame of the goggles provides an independent power source for the electrical components of the goggles. Besides solar cell other means of energy harvesting could be used, for example receiving means (e.g. a RF receiver) could be used to receive power (for e-Skin) from a corresponding transmission means (e.g. an RF transmitter) that may also transmit energy instead of only information data. Further, kinetic energy conversion means, as e.g. used in watches, may be provided for converting movements of the goggles into electrical power.

According to a further embodiment, sensing means are provided for sensing physical or physiological parameters of the user and/or physical parameters of the user's environment. Various sensors can be used as such sensing means for various purposes, and the sensing means may be attached to or integrated into the goggles, the user's clothes or the user's body. Generally, quantities like orientation and depth are preferably derived from dedicated sensors or through sensor fusion.

According to advantageous embodiments of the proposed goggles, said sensing means comprise one or more of a measurement means for measuring the user's stroke frequency, time, efficiency, depths, heartbeat, hip rotation or hip orientation, an acceleration sensor for measuring the acceleration and/or the movement of the goggles, a magnetometer, a gyroscope, a position sensor, an orientation sensor for determining the orientation of the user's head, and a magneto sensor for measuring the direction of movement of the user.

According to a further embodiment, the sensing means are integrated in the frame or a strap which is connected to the frame. This provides a comfortable solution to integrate the sensing means, since no additional straps or the like are necessary to connect the sensors to the body of the user and since parameters like the heartbeat can be measured easily at the temple of the head of the user.

For instance, an acceleration sensor provides comfortable input means to change a modality by tapping the goggles and in particular to change the modality by head movements. Thus, easy and comfortable input means are provided, which could also serve as measurement means to determine head movements of the user.

According to an embodiment of the system according to the second aspect of the invention, the feedback means comprise determining means provided to determine at least one physical and/or physiological parameter of the user. This embodiment enables the user to get feedback without involving a second person e.g. a coach.

According to a further embodiment of the system the feedback means comprise input means adapted to provide messages and/or information from a second user to the goggles. This enables a second person to communicate continuously with the user to increase the training effect.

According to a further embodiment of the system processing means are provided for processing the signals of the feedback means and for providing a processed signal to the transmission means. Thus, the processing means provides a signal, which is understandable, easier and increases the comfort of the feedback provided by the goggles.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1A:
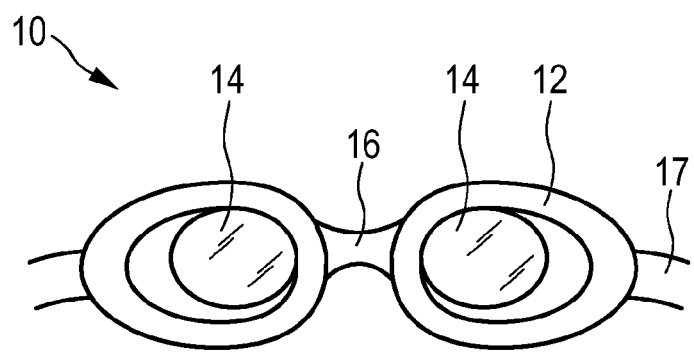
FIG. 1 shows a schematic view of the principle layout of goggles and glasses used for the goggles.

FIG. 1a shows a schematic view of goggles or glasses, which are used by swimmers. The goggles are generally designated by 10. The goggles 10 comprise a frame 12, two transparent portions 14 forming glasses 14 or lenses 14 of the goggles 10 (or at least a portion of at least one glass or lens of the goggles). It shall be noted here that the term "glass" when used herein shall be understood as including also "lens" of the goggles. The frame 12 is formed of two separate portions, which are connected to each other by means of a connecting portion 16. The two portions of the frame 12 are connected to a strap 17 provided in order to fix the goggles 10 to a head of the user.

The frame 12 of the goggles 10 is provided in order to support the glasses 14 or lenses 14 and to seal the eyes of the user with respect to the outside. The transparent portions 14 form glasses 14 or lenses 14 to provide visibility to the outside.

Figure 1B:
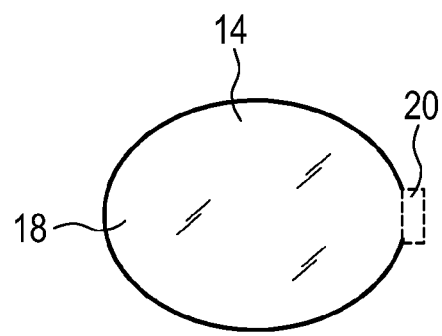

FIG. 1b shows a schematic plan view of a glass 14 of the goggles 10. The glass 14 or lens 14 can be formed by any transparent rigid material. A transparent material formed by a transparent layer or foil is attached to the surface of the glass 14 forming display means 18. The glass 14 further comprises drive means 20, coupled to the display means 18 to provide signals to the display means 18.

Figure 1C:
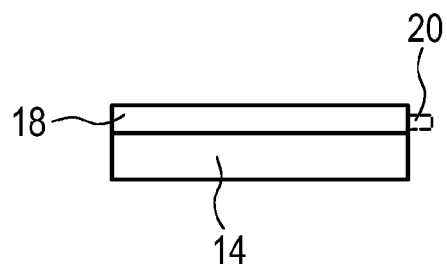

FIG. 1c shows a schematic sectional side view of the glass 14 comprising the display means 18 and the drive means 20. The display means 18 are formed of a transparent layer attached to the surface of the glass 14. The drive means 20 are coupled to the display means 18 at one lateral side thereof.

The drive means 20 provide signals to the display means 18 in order to display or present corresponding light signals to the eyes of the user.

Preferably, the light emitted by the display means 18 is shielded/made invisible in direct path. For this purpose the (at least) non-transparent portion of the glass 14 obscures between point of light emission and eyes, or alternatively, an additional shielding means is provided.

According to one embodiment of the present invention, the display means 18 are provided as a light guide 18a formed of a transparent material like PMMA or polycarbonate. The drive means 20 are provided as a light source 20a preferably formed by one or more LEDs. The light source 20a provides light signals coupled into the light guide 18a of the display means 18 in order to provide the light signals to the eyes of the user. The light guide 18a comprises outcoupling structures 22 or scattering particles 22 in order to scatter the light in the light guide 18a to provide a uniform light distribution.

In such embodiment, the known Lightskin technology may be used as such light guide, which Lightskin technology is based on the use of a light guide formed on a thin sheet of transparent material. Details of this Lightskin technology can, for instance, be found in WO 2008/065614 A1 (PH006909) and European patent application 09177884.5 (PH014332).

According to an alternative embodiment of the present invention, the display means 18 are formed of an active layer, film or foil 18b, wherein the transparency and/or the color of the layer is adaptable electrically. This active foil 18b is based on the electrophoresis, electrochromism or electrowetting effect. The drive means 20 provide an electrical signal to the display means 18 in order to change the transparency and/or the color of the display means 18 to present corresponding light signals to the eyes of the user. The foil 18b is continuously transparent, i.e. the transparency is changed but the foil 18b remains at least partially transparent.

In such an embodiment, the known eSkin technology may be used as such active layer, which eSkin technology is based on in-plane electrophoresis. Details of this eSkin technology can, for instance, be found in the Philips research technology magazine "Password", Issue 36, November 2009, pages 23-25, e.g. published at http://www.research- .philips.com/password/download/password_36.pdf. Further details may be found K.-M. H. Lenssen, M. H. W. M. van Delden, M. Müller and L. W. G. Stofmeel, "Bright Color Electronic Paper Technology and its Applications", Proc. IDW'09, pp. 529-532 (2009) and K.-M. H. Lenssen, P. J. Baesjou, F. P. M. Budzelaar, M. H. W. M. van Delden, S. J. Roosendaal, L. W. G. Stofmeel, A. R. M. Verschueren, J. J. van Glabbeek, J. T. M. Osenga and R. M. Schuurbiers, "Novel Concept for Full-Color Electronic Paper", J. of the SID 17/4, pp. 383-388 (2009). The details of eSkin technology described in these documents are herewith herein incorporated by reference.

The active foil 18b may consist of an oily liquid comprising charged, colored particles. This electrophoretic suspension is sandwiched between two substrates. At least one of these substrates contains one or more electrodes. The charged particles are moved by an electrical field generated by an electrical voltage applied to the electrodes. The charged particles are moved in the plane of the active foil 18b in order to change the transparency and/or color of the active foil 18b. If the particles are distributed over the whole area, the active foil 18b has the color of the particles. If the particles are collected in a small area fraction by means of the electrical field of the electrode, the active foil 18b is transparent. Preferably one of the electrodes is formed honeycomb shaped in plane view. Preferably, colored particles are used, which are small compared to the wavelength of the light. This allows the user to look through the glasses 14 even in a state of low transparency, similarly to sunglasses. Further, it allows the use of the subtractive color scheme to realize multi-color. In a further embodiment the compartments and/or electrodes in the foil have an a-periodic structure to avoid Moiré effects.

In a further embodiment two, three or more of these electrophoresis foils are arranged as stacked layers and attached to the surface of the glasses 14 in order to realize multi-color display means 18. Alternatively, since it is possible to control more than one type of colored particles independently, a multi-color foil can be realized as a single layer without stacking two or more different foils.

According to this embodiment, the drive means 20 provide an electrical voltage to the electrodes of the active foil 18b in order to change the light passing through the glass 14 to present corresponding light signals to the eyes of the user. The advantage of this active foil 18b is the low power consumption, since the ambient light is used or modulated and, further, a uniform light distribution due to the use of the ambient light.

According to a further embodiment, the goggles are provided with a solar cell as power source for providing electrical power to the electrical components of the goggles 10. Further, the electrical power may be provided by a device incorporated in the frame 12 harvesting kinetic energy. Thus, the movement of the goggles provides electrical power.

Further, the frame 12 may comprise acceleration measurement means for measuring the acceleration and/or the movement of the goggles 10, e.g. to change the modality. For instance, different parts of the glass can be used for different information.

Figure 2:
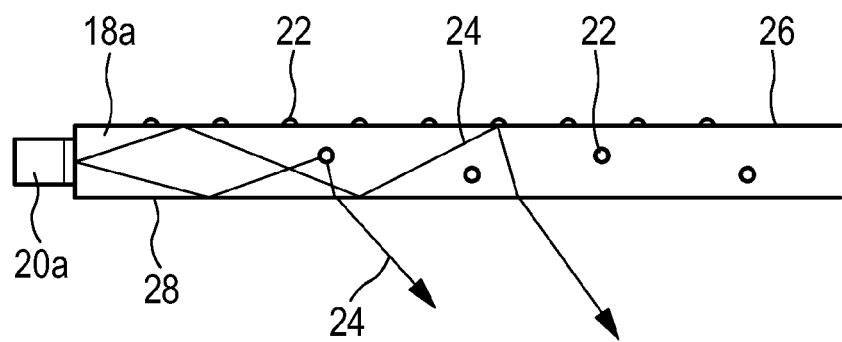
FIG. 2 shows a schematic sectional side view of light guiding means comprising drive means and outcoupling structures.

FIG. 2 shows a schematic sectional side view of a light guide 18a. The light guide 18a comprises outcoupling structures 22 to scatter light beams 24 provided by the drive means 20, formed of a light source 20a and particularly of an LED. The light guide 18a comprises an outer surface 26 and an inner surface 28. The outcoupling structures 22 or the scattering particles 22 are formed on the outer surface 26 of the light guide 18a and/or in the bulk of the light guide 18a. The glass 14 (not shown in FIG. 2; see FIG. 1c) of the goggles 10 is preferably attached to the inner surface 28 of the light guide 18a, but it can generally also be attached to the outer surface of the light guide.

The outcoupling structures 22 are provided to scatter the light beams 24 and to direct the light beams 24 to the inner surface 28 and to the eyes of the user or to direct the light beams 24 to the outer surface 28 and to other people, e.g. a coach. The light beams 24 are guided in the light guide 18a lossless via total internal reflection until they hit an outcoupling structure 22, which scatter the light beam 24 so that it can exit the light guide 18a. Thus, the scattering particles 22 provide a uniform light distribution provided to the user and/or other people. The outcoupling structures 22 are preferably provided at the outer surface 26, which is the water side of the goggles 10. The reason for this is that in the case where paint dots are used as outcoupling structures, usually more light is scattered to the direction opposite the side of the dots (which is in this case towards the eyes of the user). However, for other types of outcoupling structures this need not apply.

Figure 3:
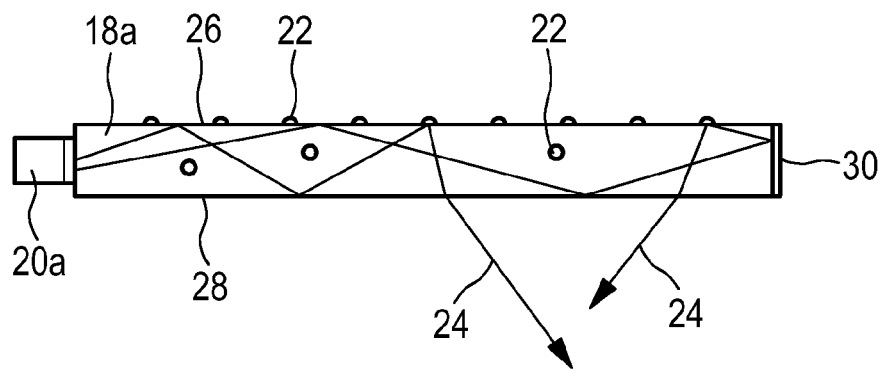
FIG. 3 shows a schematic sectional side view of light guiding means including drive means and a reflecting portion.

FIG. 3 shows a schematic sectional side view of the light guide 18a. The light guide 18a is almost identical with the light guide 18a of FIG. 2. At one edge of the light guide 18a opposite to the drive means 20 a reflective portion 30 is attached to the light guide 18a. The light beams 24, which are coupled through the light guide 18a and not scattered at a scattering particle 22 are reflected by the reflecting portion 30. Thus, the light beams 24 are directed back into the light guide 18a, whereby the efficiency of the light guide 18a is increased. The reflecting portion 30 may be formed of a mirror or a highly reflective coating or formed by roughening the outer edge, which would also result in back scattering of the light into the light guide 18a. This effect is reduced when the light guide 18a is used in the water due to the smaller difference in refractive indices between the light guide material and the water.

To increase the uniformity of light, the distance between the outcoupling structures 22 and the size of the outcoupling structures 22 can be varied over the light guide 18a, such that all areas of the glass 14 will light up with the same intensity. To obtain a homogeneous outcoupling of the light over the entire surface of the light guide 18a, the scattering particles 22 close to the light sources may be less dense than the outcoupling structures 22 farther away from the light sources 20a. The outcoupling structures 22 typically cover 10 to 15% of the surface of the light guide 18a. The outcoupling structures 22 can comprise paint dots or may be formed of local surface roughness or small recesses formed in the surface of the light guide 18a.

Further, the frame 12 can be formed of white semi-transparent rubber and the LEDs can be arranged at the frame such that the light is also diffused by the frame 12 of the goggles 10.

The light guide 18a or the active foil 18b may cover the whole surface of the glass 14 or may cover the glass 14 at least partially as described below.

Figure 4:
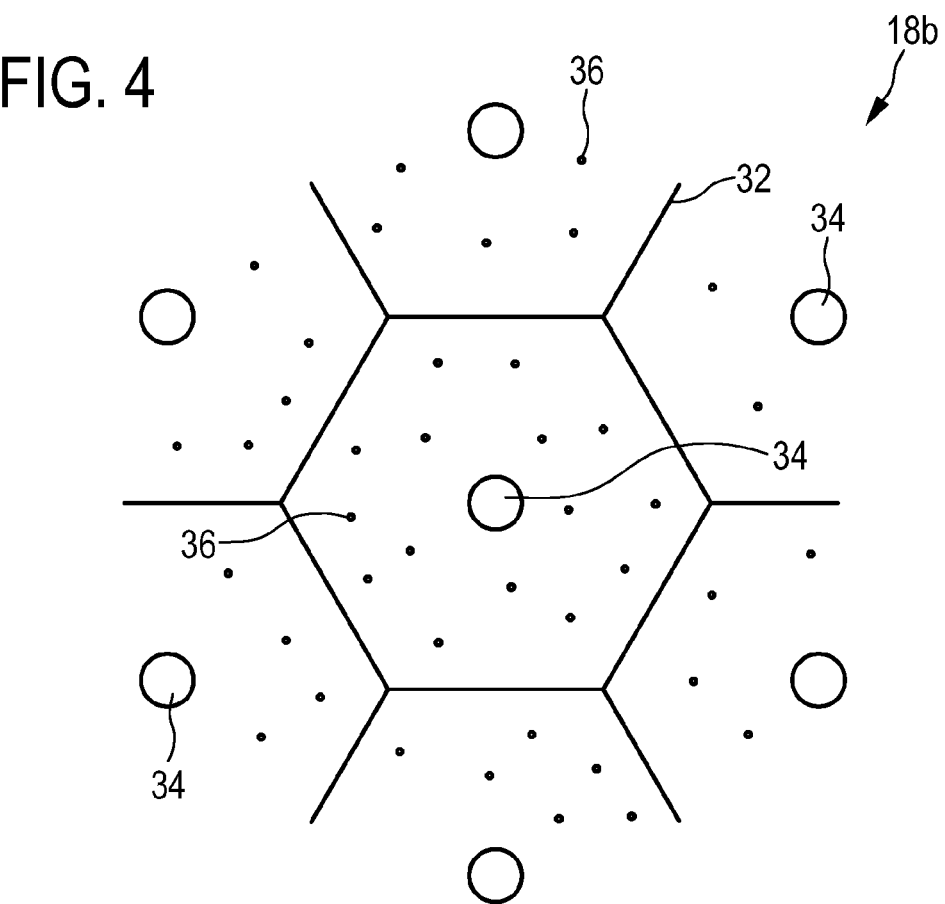
FIG. 4 shows an electrode structure of an electrophoresis foils in plan view.

FIG. 4 shows the electrode structure of the active foil 18b schematically. This active foil 18b comprises two electrodes 32, 34. One of the electrodes 32 is formed as a honeycomb shaped web and the other electrode 34 is formed circle shaped and disposed in the middle of each of the honeycomb portions of the electrode 32. The active foil 18b comprises an oily liquid 35 including charged, colored particles 36. If no electrical voltage is applied to the electrodes 32, 34 the particles 36 are distributed within the liquid 35 homogeneously, whereby the transparency of the layer is reduced. If a voltage is applied to the electrodes 32, 34 the particles 36 are attracted to one or both of the electrodes 32, 34 and the transparency is increased. Thus, the color and/or the transparency of the active foil 18b can be adapted by applying an electrical voltage to the electrodes 32, 34. The electrode 32 may have any web structure, e.g. square shaped, triangle shaped, etc.

Figure 5:
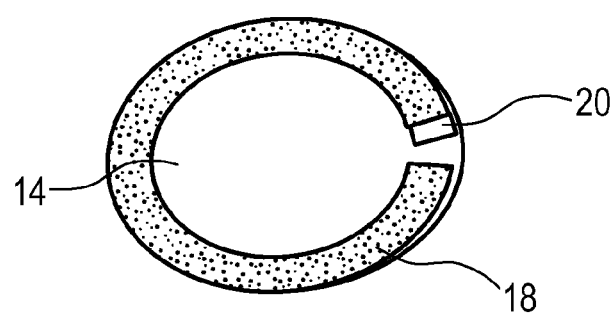
FIG. 5 shows a schematic plan view of a glass of the goggles comprising display means attached to the surface of the glass.

FIG. 5 shows the glass 14 in plan view covered partially with the display means 18. The display means 18 are formed of a curved-thin foil attached to the glass 14 at the outer edge thereof. The drive means 20 are located at one end of the circle shaped thin foil strip to provide a signal to the display means 18.

In one embodiment the drive means 20 are formed of at least one LED and the light emitted from this LED is coupled or emitted into the light guide 18a. The light guide 18a is provided with outcoupling structures 22 at the surface. The light guide 18a can be formed of a flexible material, e.g. silicone, and may be covered by a protective layer.

In an alternative embodiment, the drive means 20 are provided as electrical voltage source 20b and the display means 18 are provided as active foil 18b, wherein the transparency or the color of this foil is adaptable electrically as described above.

In an alternative embodiment, the light guide 18a is covered by a reflective portion, layer or foil to reflect the light of the light source 18a. In this embodiment, the light guide 18a does not comprise individual outcoupling structures necessarily.

Thus, even by a partially covered glass 14, the light signal can be provided in a uniform distribution to the eyes of the user.

Figure 6:
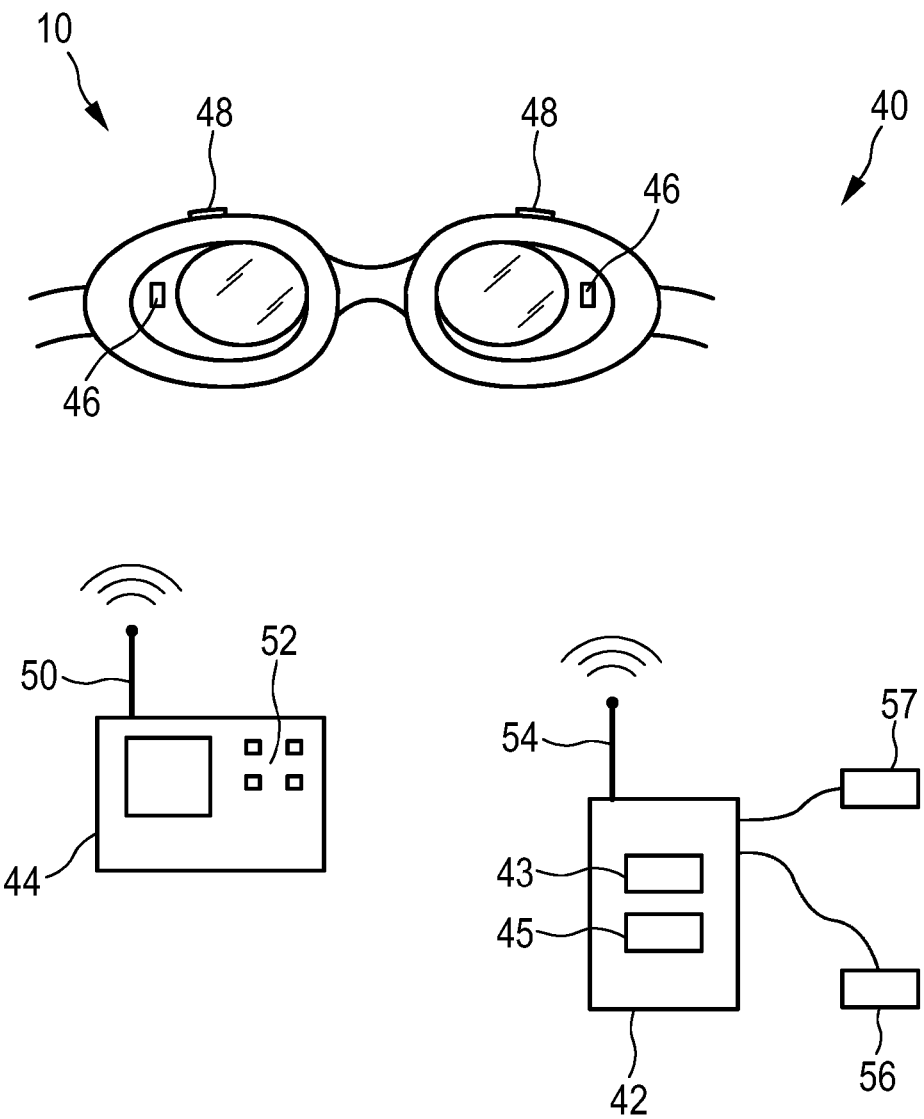
FIG. 6 shows a system comprising goggles, measurement means and input means.

FIG. 6 shows a feedback system generally designated by 40. The system 40 includes goggles 10 as described above and, further, measurement or determining means 42 and/or input means 44. The goggles 10 are generally identical with the goggles 10 described above and further including receiving means 46 for acquiring or receiving signals from the input means 44 and/or the measurement means 42. The goggles 10 further comprising solar cells 48 for providing electrical power to the electrical components.

The input means 44 are provided with transmitting means 50 to transmit signals from the input means 44 to the receiving means 46 of the goggles 10. The input means 44 are provided with a keyboard 52 or other input devices 52 to enter messages, which should be displayed or presented to the user by means of the goggles 10.

Thus, the system 40 can be used to provide feedback to the user, in particular to the swimmer using the goggles 10 and the coach using the input means 44 can send messages via the transmitting means 50 to the receiving means 46. The messages of the coach are provided by means of light signals presented by the display means 18 of the goggles 10 to the user.

The measurement means 42 are preferably provided with transmitting means 54, e.g. an RF transmitter or a cable transmitter, to transmit signals to the receiving means 46 of the goggles 10. The measurement means 42 further comprise measurement devices 56 to measure physical or physiological parameters of the user, in particular the swimming user, e.g. stroke frequency, time, efficiency, depths, heartbeat, hip rotation or hip orientation, etc. The measurement devices 56 are formed of sensors which may be arranged anywhere at the body of the user, in particular incorporated in the clothes, or attached to the body as on-body sensors, or which may be integrated in any way into the goggles, in which case no RF transmitter is needed, but a cable transmission is preferably used.

Further, various sensors 57 for sensing physical parameters of the user's environment may be provided. Also these sensors may be arranged anywhere at the body of the user, in particular incorporated in the clothes, or attached to the body as on-body sensors, or which may be integrated in any way into the goggles. Said sensors 57 may include one or more of an acceleration sensor for measuring the acceleration and/or the movement of the goggles, a magnetometer, a gyroscope, a position sensor, an orientation sensor for determining the orientation of the user's head (generally, the orientation may also be derived from other signals obtained by other sensors, e.g. from signals of an acceleration and/or magneto sensor), and a magneto sensor for measuring the direction of movement of the user.

For instance, an acceleration sensor may be used to easily change a modality by tapping the goggles and in particular to change the modality by head movements.

Further, a sensor for measuring the orientation of the head may be provided. Signal processing may deduce movement parameters of the other body parts, possibly using additional knowledge (e.g. assumptions constraining the ways the signals can be interpreted).

Further, a sensor for heart rate measurement may be provided, e.g. using existing optical methods, attached or as part of the goggles such that they measure at the temples at the sides of the eyes.

Still further, a magneto sensor on the goggles may be provided to assess the right direction of where the user is going.

In general, various sensor and sensing modalities may be used according to the present invention, including the use of magnetometers, gyroscopes, and position sensitive sensors like radio based sensors.

In a preferred embodiment one or more actuators are provided beyond the one or more LEDs, e.g. to move the LEDs for modifying/modulating the light signals issued by the one or more LEDs. In particular, vibrating/tactile transducers can be used for this purpose.

The measurement means 42 uses the data provided by the sensing means, i.e. the measurement devices 56 and the sensors 57, and processes the data by means of processing means 43 using background knowledge stored in storing means 45 and provides a processed signal by using the transmitting means 54 to the receiving means 46 to present feedback signals to the user by means of the goggles 10.

Thus, the system 40 can provide feedback from a second person, e.g. the coach and/or from the measurement means 42 measuring physical and/or physiological parameters.

For energy supply other means may be provided rather than the solar cell 48. For instance, the receiving means 46 could be used to receive sufficient energy by RF transmission from the transmission means 50. Further, other embodiments for energy supply exist, such as a (rechargeable or non-rechargeable) battery.

Figure 7:
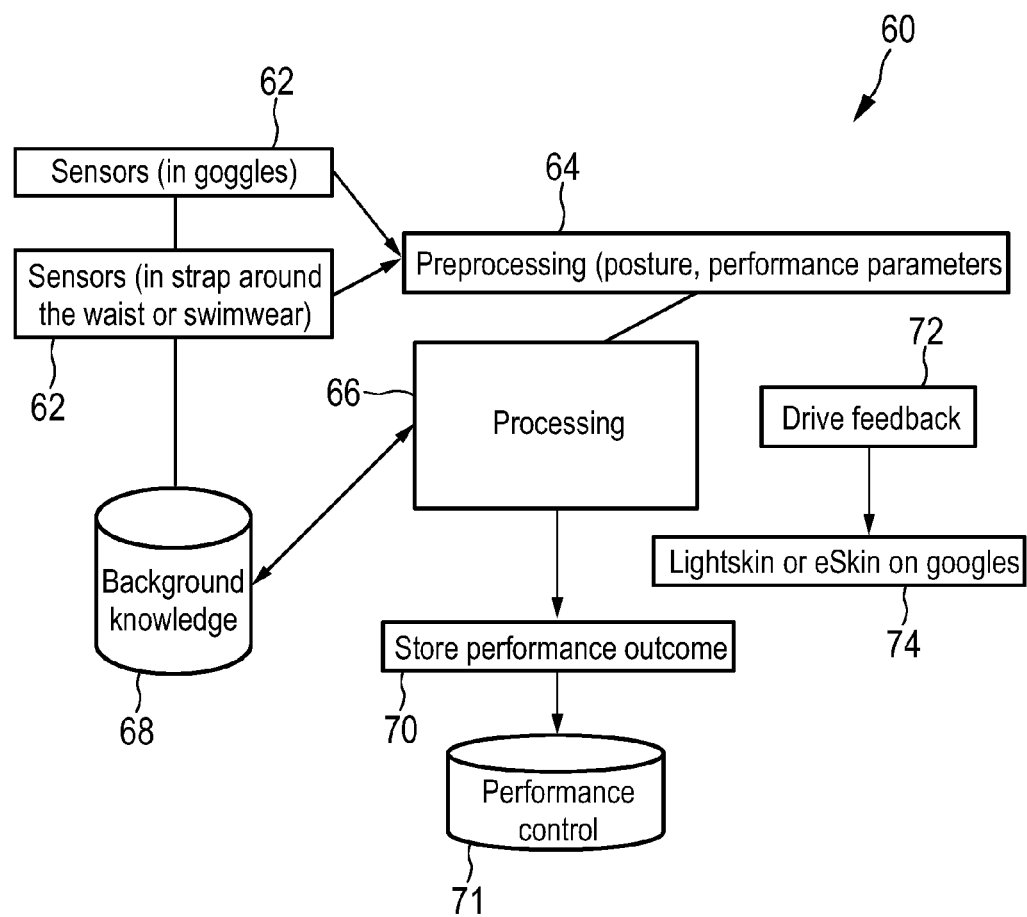
FIG. 7 shows a flow diagram illustrating a method for processing and presenting feedback to the user.

FIG. 7 shows a flow diagram illustrating a method 60 for presenting feedback to a user. Sensors (i.e. the measurement means 56 and/or the sensors 57) provided in the goggles 10 and/or at the body of the user determine (62) physical or physiological parameters and provide the measured data preferably to processing means for preprocessing (64). The preprocessed data is provided to further processing means for processing (66) of the data by using background knowledge 68. The processed data may be stored (70) in a storing means for evaluation or performance control 71. The processing means provide feedback (72, 74) to the display means 18 of the goggles 10. The data to be measured may be transmitted directly to the processing means for processing (66) and may be displayed by the input means 44. The coach can control the feedback to the user either by sending commands to a processor system located at the user or by controlling the signal or information sent to the receiving means 46 of the goggles 10 and presented to the user.

Figure 8:
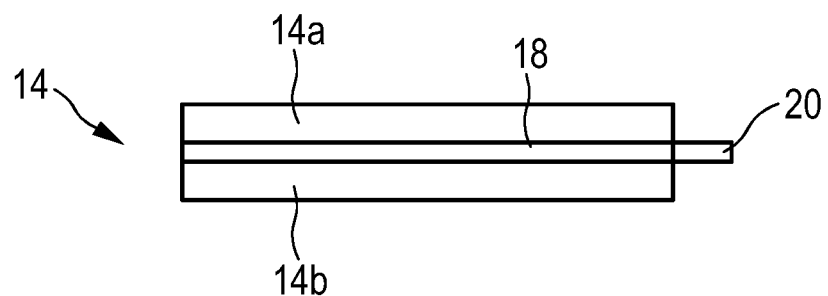
FIG. 8 shows a schematic sectional side view of light guiding means stacked between two portions of the glass.

FIG. 8 shows a further embodiment of the transparent portion 14 used for the goggles 10. The transparent portion 14 is formed of two separate transparent layers 14a, 14b or glass portions 14a, 14b. The display means 18 are stacked or sandwiched between the transparent layers 14a, 14b or the glass portions 14a, 14b. The drive means 20 are coupled to the display means 18 as described above. The display means 18 according to this embodiment can be formed of a light guide 18a or an active foil 18b as described above. Thus, the display means 18 are mechanically protected between the two glass portions 14a, 14b.

Figure 9:
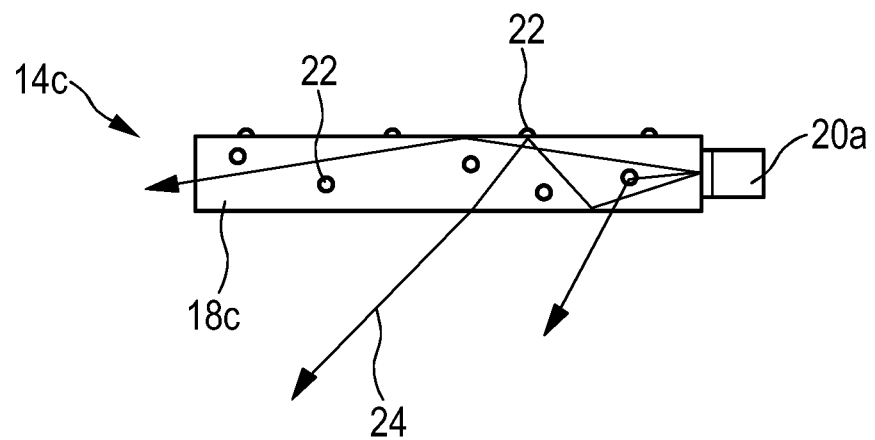
FIG. 9 shows a schematic sectional side view of light guiding means integrated in the glass.

FIG. 9 shows a further embodiment of the transparent portion 14 used for the goggles 10. The transparent portion 14c or the glass 14c of the goggles 10 according to this embodiment forms the light guide 18c. The transparent portion 14c or the glass 14c is formed of a rigid transparent material, wherein the light source 20a is coupled to the transparent portion 14c to inject the light beams 24 into the transparent portion 14c. The transparent portion 14c comprises outcoupling structures 22 to scatter the light beams 24 as described above. Thus, the light guide 18c is integrated in the transparent portion 14c.

In summary, the present invention provide goggles, a system and a method for providing feedback to a user that is more comfortable for the user.

Figure 10:
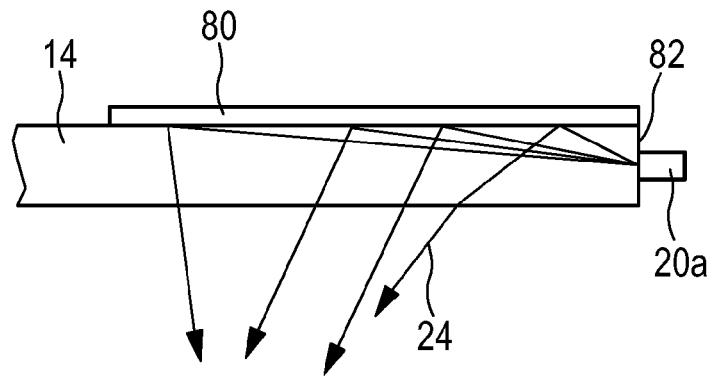
FIG. 10 shows a schematic side view of a glass covered by a reflective portion.

FIG. 10 shows a schematic sectional side view of the transparent portion 14 according to a further embodiment of the invention. The transparent portion 14 or the glass 14 of the goggles 10 according to this embodiment forms the light guide. The transparent portion 14 or the glass 14 is formed of a rigid transparent material, wherein the light source 20a is coupled to the transparent portion 14 to inject the light beams 24 into the transparent portion 14. The transparent portion 14 is covered partially by a reflective portion 80 or a diffusely reflective portion 80. The reflective portion 80 is formed of a continuous layer, foil or paint. The reflective portion 80 is preferably formed on a surface of the transparent portion 14 and located at an edge 82 of the glass 14. According to this embodiment, the light 24 of the light source 20a is guided through the transparent portion 14 and reflected preferably diffusely reflected or reflectively scattered from the reflective or diffusely reflective portion 80 to the eye of the user. Thus, the display means according to this embodiment provide an easy and effective solution to provide light signals to the user.

Figure 11:
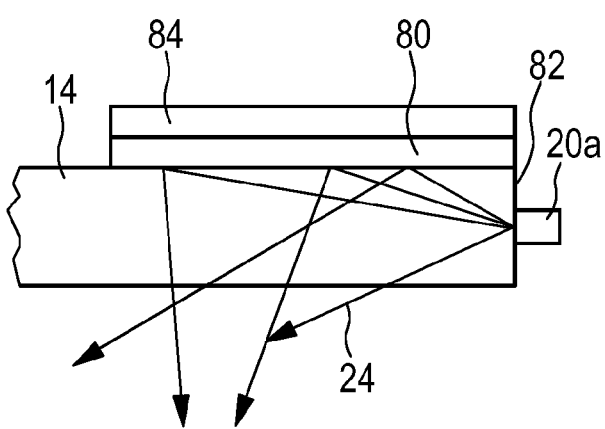
FIG. 11 shows a schematic sectional side view of a glass having a protective layer.

FIG. 11 shows a schematic sectional side view of the transparent portion 14 according to the embodiment of FIG. 10. Identical elements are denoted by identical reference numerals, wherein here only the differences are explained in detail. The reflective portion 80 or diffusely reflective portion 80 is covered by a protective layer 84 to protect the reflective portion 80 from environmental influences, in particular water, so that the robustness of the display means and, in particular, of the reflective portion 80 is improved.

The protective layer 84 can be used for all embodiments of the present invention to improve the robustness of the goggles in general.

Figure 12:
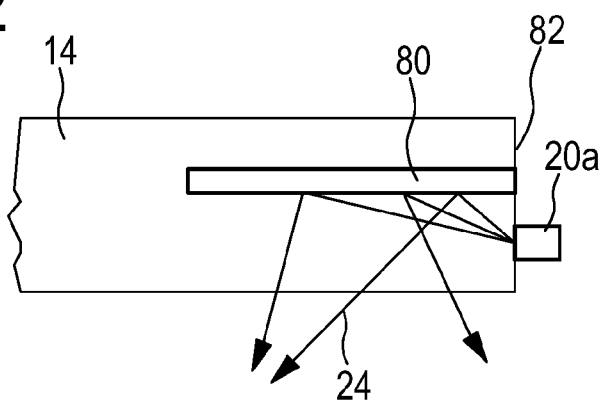
FIG. 12 shows a schematic sectional side view of a glass having an integrated reflective portion.

FIG. 12 shows a schematic sectional side view of the transparent portion 14 or the glass 14 according to a further embodiment of the present invention. The transparent portion 14 comprises the reflective portion 80 or the diffusely reflective portion 80, which is integrated in the transparent portion 14. The light source 20a is coupled to the transparent portion 14 on one side of the reflective portion 80, so that the light 24 of the light source 20a can be reflected or diffusely reflected or reflectively scattered by the reflective portion 80 and directed or guided to the eye of the user. Since the reflective portion 80 is integrated in the transparent portion 14, the robustness of the glass 14 of the goggles is further improved.

In general, the reflective portion 80 or diffusely reflective portion 80 can be formed of a layer or foil or reflective paint and is usually not transparent, so that this part of the glass 14 does not transmit light from the outside to the eyes of the user.

Figure 13:
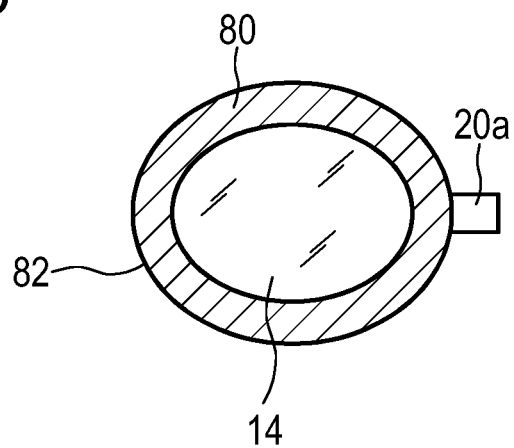
FIG. 13 shows a schematic plan view of a glass of the goggles comprising a reflective portion partially covering the glass.

FIG. 13 shows the glass 14 or a lens 14 in a plan view covered partially by the reflective or diffusely reflective portion 80. The reflective portion 80 is formed cycle-shaped at the outer edge 82 of the glass 14. The reflective portion 80 may be formed as an entire circle, as a semicircle or a portion at one side of the glass 14. The light source 20a is located at one side of the glass 14 to provide the light signals to the transparent portion 14 and the reflective layer 80.

Figure 14:
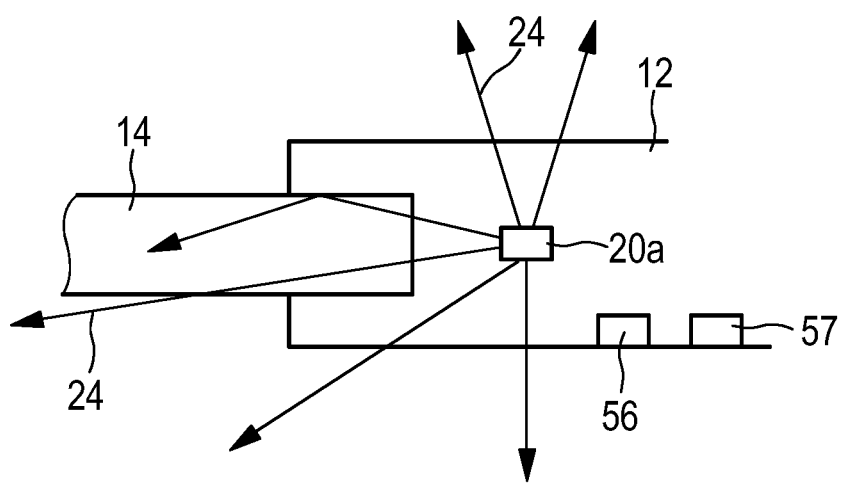
FIG. 14 shows a schematic sectional view of a glass of the goggles attached to a frame having an integrated light source.

FIG. 14 shows an alternative embodiment of the present invention. The glass 14 is attached to the frame 12. The light source 20a is integrated in the frame 12. The frame 12 is partially formed of a transparent material, so that the light 24 can be guided from the light source 20a to the transparent portion 14 and to the eye of the user. Further, since the frame 12 is formed partially of a transparent material, the light 24 is also coupled to the outside of the goggles 10 to provide the light signals to other persons like a coach. Hence, the goggles according to this embodiment can be used to provide feedback either to the user or other people.

The measurement means 56 and/or sensors 57 of FIG. 6 can also be integrated in the frame 12 and/or in the strap 17 to measure physical or physiological parameters, in particular the stroke frequency, time, efficiency, depth, heartbeat, hip rotation or hip orientation, etc. The advantage of the integration of the measurement means 56 and/or sensors 57 in the frame 12 or the strap 17 is that it is comfortable to use and physiological parameters like the heartbeat can be easily measured at the temple of the head.

In an alternative embodiment, the light source 20a is integrated in the strap, in particular to provide light signals to other people.

The frame 12 is preferably formed of transparent and/or flexible material like silicon and serves as a light guide to guide the light of the light source 20a to the outside or to the glass 14.

In a further embodiment, the connecting means 16 and/or the straps 17 may serve as the light guide. In this case, the connecting means 16 and/or the strap are at least partially transparent and cover the frame 12 and/or at least one glass 14 at least partially. In this case, the connecting means 16 and the strap 17 may be connected to each other or formed of one continuous strap.

Figure 15:
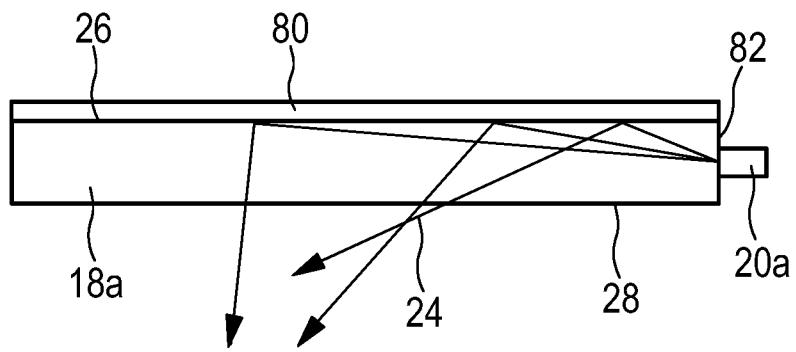
FIG. 15 shows a light guide having a reflective portion.

FIG. 15 shows a schematic sectional side view of a further embodiment of the light guide 18a. The light guide 18a is covered by the reflective or diffusely reflective portion 80 to reflect the light beams 24 emitted from the light source 20a. The light source 20a is preferably formed as an LED. The light guide 18a comprises the outer surface 26 and the inner surface 28. The reflective portion 80 is formed on the outer surface 26 of the light guide 18a. The glass 14 (not shown in FIG. 15; see FIG. 1c) of the goggles 10 is preferably attached to the inner surface 28 of the light guide 18a. The light beams 28 are guided by the light guide 18a to the eyes of the user and reflected by the reflective portion 80 to increase the efficiency of the light source 20a.

The light guide 18a is preferably formed of a flexible material like silicone and can be attached to the glass 14 by means of an adhesive.

Figure 16:
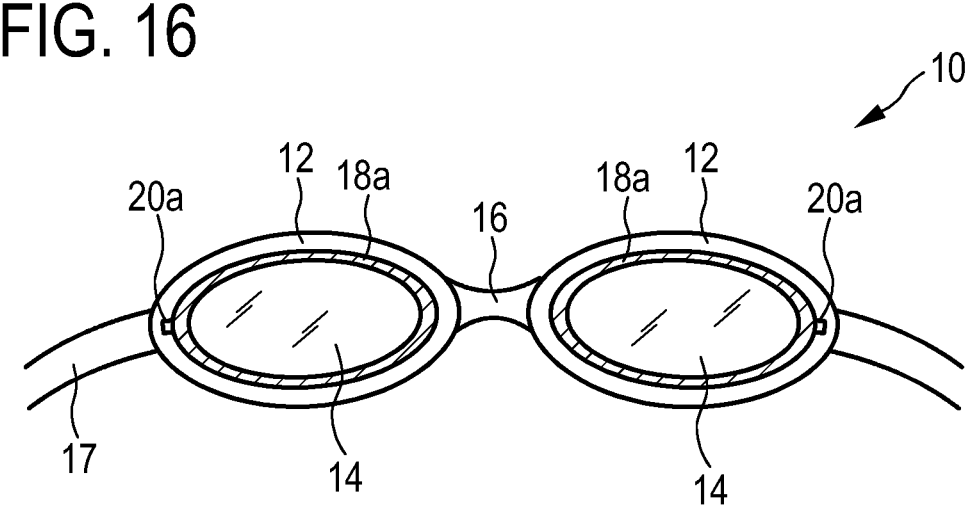
FIG. 16 shows a schematic view of a frame of the goggles having light guiding means around the glasses.

FIG. 16 shows a schematic view of the goggles including the frame 12 supporting the glasses 14 or lenses 14, wherein the light guides 18a are attached to a surface of the frame 12. The light guides 18a are arranged around the glasses 14 or lenses 14 to provide a uniform light distribution to the eyes of the user. In particular, the frame 12 may be formed of a transparent material to guide the light emitted from the light source 20a and guided through the light guide 18a to the inside of the goggles 10.

In an alternative embodiment, the light guides 18a can be formed as a semi-cycle or a portion attached to the frame 12 at one side of the glass 14. The frame 12 can be formed of a flexible material like silicone.

While the present invention is described above using swimming goggles, the invention may also be used for other sports where goggles are used, like cycling, skiing, skating, diving, snorkeling and possibly any outdoor sport where sunglasses are used e.g. golf, jogging, etc.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. Goggles, configured for an exercise activity, for providing feedback to a user, the goggles comprising:
   a lens;
   a display comprising:
      a first surface of the display being arranged to continuously cover all of a first surface of the lens in order to uniformly distribute light across all of the first surface of the lens;
      a second surface of the display being exposed; and
      a light guide to render light signals;
   a light source coupled to the display to generate signals to the display corresponding to the light signals to be displayed, wherein the display is at least partially formed of a frame or frame connection connected to the lens, the frame and/or the frame connection being formed at least partially of a transparent material; and
   at least one outcoupling structure located at the display to scatter the light signals.

2. The goggles as claimed in claim 1, wherein the at least one outcoupling structure is formed on the light guide such that the light signals are enabled to exit the light guide through the at least one outcoupling structure.

3. The goggles as claimed in claim 1, wherein the light guide comprises an at least partially reflective portion or an at least partially diffusely reflective portion for reflecting and/or scattering the light of the light source.

4. The goggles as claimed in claim 1, wherein the at least one outcoupling structure is formed at either the first or second surface and/or in a bulk of the lens.

5. The goggles as claimed in claim 1, further comprising an energy supply to provide electrical power, a receiver configured to obtain electrical power via contactless energy transfer and/or a kinetic energy convertor to convert movements of the goggles into electrical power.

6. The goggles as claimed in claim 1, further comprising a sensor to sense physical or physiological parameters of a user and/or physical parameters of an environment of the user.

7. The goggles as claimed in claim 6, wherein said sensor is further configured to:
   measure a stroke frequency of the user, time, efficiency, depths, heartbeat, hip rotation or hip orientation;
   measure an acceleration and/or movement of the goggles;
   determine the orientation of a head of the user; and
   measure a direction of movement of the user.

8. The goggles as claimed in claim 6, wherein said sensor is integrated in the frame or a strap of the goggles which is connected to the frame.

9. The goggles as claimed in claim 1, wherein the display comprises a liquid including charged, colored particles for changing a transparency and/or the color of the display.

10. The goggles as claimed in claim 1, further comprising at least one receiver to acquire signals to be displayed.

11. A system for providing feedback to a user, comprising:
   a feedback system configured to provide a feedback signal;
   a transmitter coupled to the feedback system, the transmitter being configured to communicate the feedback signal to a receiver coupled to goggles for an exercise activity, the goggles comprising:
      a lens;
      a display comprising:
         a first surface of the display being arranged to continuously cover all of a first surface of the lens in order to uniformly distribute light across all of the first surface of the lens;
         a second surface of the display being exposed; and
         a light guide to render light signals;
      a light source coupled to the display or the lens for providing signals to the display corresponding to the light signals to be rendered, wherein the display is at least partially formed of a frame or frame connection, the frame and/or the frame connection being formed at least partially of a transparent material; and
      at least one outcoupling structure located at the display to scatter the light signals.

12. The system as claimed in claim 11, wherein the feedback system further comprises at least one sensor to determine at least one physical and/or physiological parameter of the user.

13. A method for providing feedback to a user, comprising:
   determining at least one physical and/or physiological parameter of the user;
   generating a feedback signal based at least partially on the at least one physical and/or physiological parameter;
   providing the feedback using goggles for an exercise activity, the goggles comprising:
      a lens;

a display comprising:
  a light guide for rendering light signals;
  a first surface of the display being arranged to continuously cover all of a first surface of the lens in order to uniformly distribute light across all of the first surface of the lens;
  a second surface of the display being exposed;
a light source coupled to the display for providing signals to the display corresponding to the light signals to be displayed, wherein the display is at least partially formed of a frame or frame connection, the frame and/or the frame connection being formed at least partially of a transparent material; and
at least one outcoupling structure located at the display to scatter the light signals.

14. Goggles, for an exercise activity, for providing feedback to a user, the goggles comprising:

a lens;
a display comprising a light guide to render light signals;
at least one outcoupling structure located at the display to scatter the light signals; and
a light source coupled to the display, the light source to generate signals to the display corresponding to the light signals to be displayed, wherein the display is formed of a continuously at least partially transparent element, a first surface of the display being continuously attached to all of the first surface of the lens in order to uniformly distribute light across all of the first surface of the lens, wherein a second surface of the display is exposed, and wherein a transparency and/or color of the display are adaptable electrically using the signals provided by the light source.

* * * * *